United States Patent
Yukikata et al.

(10) Patent No.: US 10,702,956 B2
(45) Date of Patent: Jul. 7, 2020

(54) FLUX ACTIVATOR, FLUX, AND SOLDER

(71) Applicant: KOKI Company Limited, Tokyo (JP)

(72) Inventors: Kazuhiro Yukikata, Tokyo (JP); Yuusuke Sato, Tokyo (JP); Junichi Aoki, Tokyo (JP); Mitsuyasu Furusawa, Tokyo (JP); Kimiaki Mori, Tokyo (JP)

(73) Assignee: KOKI COMPANY LIMITED, Tokyo (JP)

( * ) Notice: Subject to any disclaimer, the term of this patent is extended or adjusted under 35 U.S.C. 154(b) by 247 days.

(21) Appl. No.: 15/546,868

(22) PCT Filed: Feb. 5, 2016

(86) PCT No.: PCT/JP2016/053540
§ 371 (c)(1),
(2) Date: Jul. 27, 2017

(87) PCT Pub. No.: WO2016/125901
PCT Pub. Date: Aug. 11, 2016

(65) Prior Publication Data
US 2018/0015576 A1    Jan. 18, 2018

(30) Foreign Application Priority Data
Feb. 5, 2015    (JP) .................... 2015-021528

(51) Int. Cl.
| | | |
|---|---|---|
| *B23K 35/36* | (2006.01) | |
| *C07C 69/63* | (2006.01) | |
| *C07C 43/17* | (2006.01) | |
| *C07C 271/28* | (2006.01) | |
| *C07C 43/176* | (2006.01) | |
| *C07C 33/42* | (2006.01) | |
| *C07C 69/76* | (2006.01) | |
| *C07C 271/16* | (2006.01) | |
| *B23K 35/362* | (2006.01) | |
| *B23K 35/26* | (2006.01) | |
| *C22C 13/00* | (2006.01) | |

(52) U.S. Cl.
CPC ........ *B23K 35/3616* (2013.01); *B23K 35/362* (2013.01); *C07C 33/423* (2013.01); *C07C 43/17* (2013.01); *C07C 43/176* (2013.01); *C07C 69/63* (2013.01); *C07C 69/76* (2013.01); *C07C 271/16* (2013.01); *C07C 271/28* (2013.01); *B23K 35/26* (2013.01); *B23K 35/262* (2013.01); *C22C 13/00* (2013.01)

(58) Field of Classification Search
CPC ... B23K 35/362; B23K 35/3616; B23K 35/36
USPC .......................................................... 148/23
See application file for complete search history.

(56) References Cited

U.S. PATENT DOCUMENTS

| | | | |
|---|---|---|---|
| 3,676,380 A | 7/1972 | McLaughlin et al. | |
| 4,342,607 A | 8/1982 | Zado | |
| 4,587,217 A | 5/1986 | Geigert et al. | |
| 6,881,278 B2 | 4/2005 | Amita et al. | |
| 9,770,786 B2 | 9/2017 | Toyoda et al. | |
| 2001/0042779 A1 | 11/2001 | Amita et al. | |
| 2002/0046627 A1* | 4/2002 | Amita ................ | B23K 35/0244 75/252 |
| 2003/0200836 A1 | 10/2003 | Amita et al. | |
| 2013/0098506 A1 | 4/2013 | Toyoda et al. | |

FOREIGN PATENT DOCUMENTS

| | | |
|---|---|---|
| CN | 103038019 | 4/2013 |
| JP | 60-203387 | 10/1985 |
| JP | 2002-086292 | 3/2002 |
| JP | 2002120089 A | 4/2002 |
| JP | 2003-025089 | 1/2003 |
| JP | 20031487 A | 1/2003 |
| JP | 2003225796 A | 8/2003 |
| JP | 2009255153 A | 11/2009 |
| JP | 201346929 A | 3/2013 |
| JP | 2013126671 A | 6/2013 |
| JP | 2013173156 A | 9/2013 |
| JP | 2014188578 A | 10/2014 |
| WO | 99/64199 | 12/1999 |
| WO | 2011151894 A1 | 12/2011 |

OTHER PUBLICATIONS

Anonymous: "India's Import Export Data", May 17, 2014, XP055481197, pp. 1-7 originally published on https://www.zauba.com/export-3+IODO+4/hs-code-29055900/p-1-hs-code.html.

* cited by examiner

Primary Examiner — Weiping Zhu
(74) Attorney, Agent, or Firm — Clark & Brody LP

(57) ABSTRACT

Provided is a flux activator containing a halogen compound represented by formula 1 below:

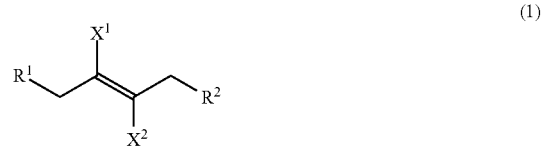

(1)

where $X^1$ and $X^2$ represent different halogen atoms, $R^1$ and $R^2$ are each a group represented by any one of formulas —OH, —O—$R^3$, —O—C(=O)—$R^4$, and —O—C(=O)—NH—$R^5$, $R^1$ and $R^2$ optionally represent the same group or different groups, $R^3$, $R^4$, and $R^5$ are each an aromatic hydrocarbon group having 1 to 18 carbon atoms or an aliphatic hydrocarbon group having 1 to 18 carbon atoms, and $R^3$, $R^4$, and $R^5$ optionally represent the same group or different groups.

3 Claims, No Drawings

FLUX ACTIVATOR, FLUX, AND SOLDER

CROSS-REFERENCE TO RELATED APPLICATIONS

This application is the United States national phase of International Application No. PCT/JP2016/053540 filed Feb. 5, 2016, and claims priority to Japanese Patent Application No. 2015-021528 filed Feb. 5, 2015, the disclosures of which are hereby incorporated in their entirety by reference.

FIELD

The present invention relates to a flux activator, and a flux and a solder containing the activator.

BACKGROUND

A solder used for joining electronic parts generally contains a solder alloy and a flux. The flux contains a modified rosin, a resin component composed of a synthetic resin or the like, and an activator, and further a solvent component and other additives, as needed. As the activator, halogen activators containing organic halogen compounds are known. For example, Patent Literature 1 discloses a flux containing, as an activator, a halogen compound in which halogen atoms such as bromine and chlorine are introduced into an organic compound by covalent bonds. Further, Patent Literature 2 discloses a flux containing an iodine-containing carboxyl compound as an activator. It is known that such a halogen compound can improve solder wettability by removing the oxide film on the surface of the solder or preventing reoxidation, and further reducing the surface tension of the solder.

However, it is difficult for the flux containing such a halogen compound activator to exert the aforementioned effects immediately after soldering, and it is also difficult to maintain the effects. Therefore, it is difficult to sufficiently improve the solder wettability in a general soldering step, which has been a problem.

CITATION LIST

Patent Literature

Patent Literature 1: JP 2002-120089 A
Patent Literature 2: JP 2014-188578 A

SUMMARY

Technical Problem

The present invention has been devised in view of the problems of the conventional arts described above, and an object thereof is to provide a flux activator, a flux, and a solder which can improve the solder wettability immediately after soldering and can continuously improve the solder wettability.

Solution to Problem

A flux activator of the present invention contains a halogen compound represented by formula 1 below, where $X^1$ and $X^2$ represent different halogen atoms, $R^1$ and $R^2$ are each a group represented by any one of formulas —OH, —O—$R^3$, —O—C(=O)—$R^4$, and —O—C(=O)—NH— $R^5$, $R^1$ and $R^2$ optionally represent the same group or different groups, $R^3$, $R^4$, and $R^5$ are each an aromatic hydrocarbon group having 1 to 18 carbon atoms or an aliphatic hydrocarbon group having 1 to 18 carbon atoms, and $R^3$, $R^4$, and $R^5$ optionally represent the same group or different groups.

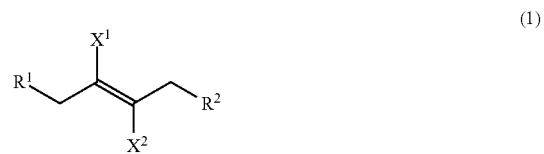

(1)

$X^1$ may be Br or I, and $X^2$ may be Br or I.

A flux according to the present invention contains the flux activator.

A solder according to the present invention contains the flux.

Advantageous Effects of Invention

The present invention can improve the solder wettability immediately after soldering and can continuously improve the solder wettability.

DESCRIPTION OF EMBODIMENTS

Hereinafter, a flux activator, a flux, and a solder according to the present invention will be described.

First, a flux activator of this embodiment will be described. The flux activator of this embodiment (which may be hereinafter referred to simply as activator) contains a halogen compound represented by formula 1 below.

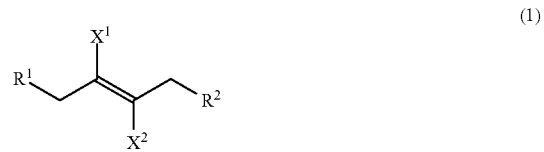

(1)

In the formula, $X^1$ and $X^2$ represent halogen atoms such as Br, I, Cl, F, and At, and are not specifically limited as long as they are halogen atoms different from each other, but are preferably Cl, Br, or I. In particular, $X^1$ and $X^2$ are preferably Br or I, respectively. That is, it is preferable that, when $X^1$ is Br, $X^2$ be I, and when $X^1$ is I, $X^2$ be Br. Specifically, a halogen compound represented by formula (2) or (3) below is preferable. However, in formula (2) and (3) below, $R^1$ and $R^2$ are each a group represented by any one of formulas —OH, —O—$R^3$, —O—C(=O)—$R^4$, and —O—C(=O)—NH—$R^5$, and $R^1$ and $R^2$ optionally represent the same group or different groups. Further, $R^3$, $R^4$, and $R^5$ optionally represent the same group or different groups, and are each an aromatic hydrocarbon group having 1 to 18 carbon atoms or an aliphatic hydrocarbon group having 1 to 18 carbon atoms. For example, $R^3$, $R^4$, and $R^5$ may be each a methyl group, an ethyl group, or a propyl group, having 1 to 6 carbon atoms; a straight chain or branched chain alkyl group having 18 carbon atoms; an alkenyl group, a cyclohexyl group, or a phenyl group, having 2 to 6 carbon atoms; or a cyclohexyl group or a phenyl group substituted with a substituent such as a methyl group, a hydroxy group, a methoxy group, a carboxyl group, an amino group, and a cyano group.

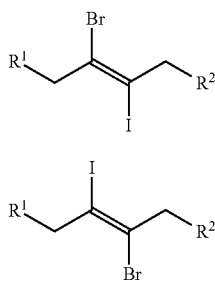

(2)

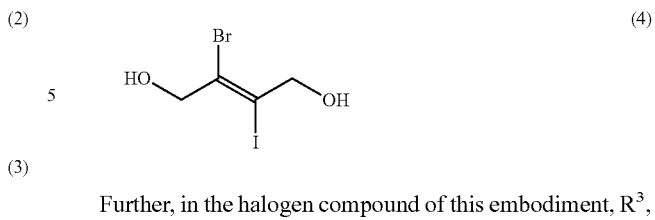

(4)

(3)

In the case where $X^1$ and $X^2$ above are a combination of Br and I, the wettability can be improved immediately after soldering, and the effect of allowing the wettability to be continuously improved is further enhanced at the same time. The reasons why the aforementioned effects are obtained when $X^1$ and $X^2$ above are halogen atoms different from each other may possibly be as follows.

The introduction of halogen atoms into the compound constituting the activator allows the oxide film on the surface of the solder to be removed or formation of the oxide film to be suppressed, due to the action of the halogen atoms, and further allows the surface tension of the solder to be reduced, so that the solder wettability can be improved. However, in the aforementioned effects exerted by the halogen atoms, the strength of the effects that can be exerted, the time required to exert the effects, the persistence of the effects, and the like, are different in each halogen atom. For example, although Br (bromine) can exert the aforementioned effects immediately after soldering, comparatively, in the halogen atoms, it has low heat resistance. Therefore, the effects decrease by heating in soldering, and there are cases where the effect of improving the wettability cannot be exerted continuously. In order to solve such a problem, it is conceivable to shorten the soldering time by raising the soldering temperature or to increase the content of Br, for example. However, when the soldering temperature is raised, thermal damage to the substrate or electronic parts increases, and further the residual flux may be burnt. Further, the increase of the content of Br may possibly cause a reduction in the insulating properties of the residual flux.

Further, although I (iodine) has high heat resistance and high persistence of the effects, comparatively, in the halogen atoms, it requires much time to remove the oxide film. Therefore, there may be cases where the wettability cannot be improved, for example, in a step of soldering in a short time.

The activator of this embodiment can exert the effect of improving the wettability immediately after soldering and can exert the effect continuously, by containing a halogen compound in which different halogen atoms are introduced.

In the halogen compound of this embodiment, $R^1$ and $R^2$ in formulas (1) to (3) above are each a group represented by any one of formulas —OH, —O—$R^3$, —O—C(=O)—$R^4$, and —O—C(=O)—NH—$R^5$. $R^1$ and $R^2$ optionally represent the same group or different groups but preferably represent the same group.

Examples of the halogen compound having $R^1$ and $R^2$ that are both the same group represented by —OH include a halogen compound represented by formula (4) below.

Further, in the halogen compound of this embodiment, $R^3$, $R^4$, and $R^5$ in formulas (1) to (3) above are each an aromatic hydrocarbon group having 1 to 18 carbon atoms or an aliphatic hydrocarbon group having 1 to 18 carbon atoms, as described above. Above all, $R^3$, $R^4$, and $R^5$ are each preferably a phenyl group.

Examples of the halogen compound having $R^1$ and $R^2$ that are both the same group represented by —O—$R^3$ and $R^3$ that is a phenyl group include a halogen compound represented by formula (5) below.

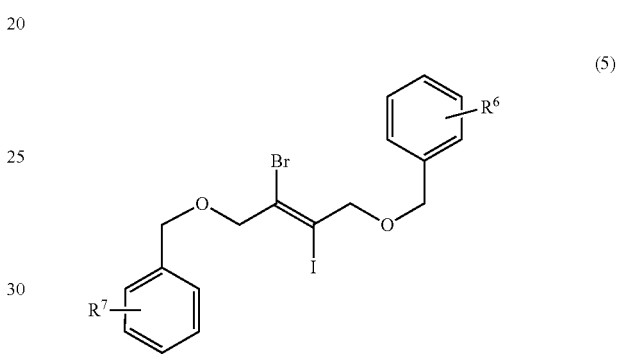

(5)

$R^6$ and $R^7$ in formula (5) above may be each a hydrogen atom, a methyl group, a hydroxy group, a methoxy group, a carboxyl group, an amino group, or a cyano group, but are each preferably a hydrogen atom or a methyl group. Further, $R^6$ and $R^7$ optionally represent the same group or different groups, but preferably represent the same group.

Examples of the halogen compound having $R^1$ and $R^2$ that are both the same group represented by —O—C(=O)—$R^4$ and $R^4$ that is a phenyl group include a halogen compound represented by formula (6) below.

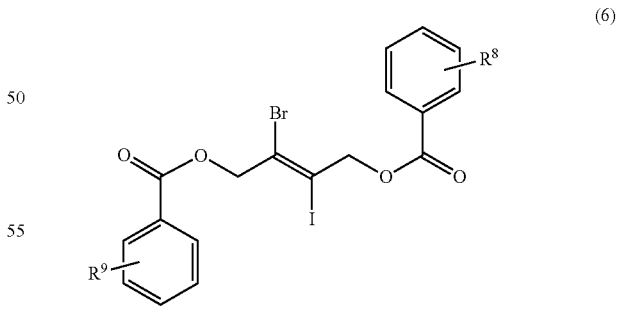

(6)

$R^8$ and $R^9$ in formula (6) above may be each a hydrogen atom, a methyl group, a hydroxy group, a methoxy group, a carboxyl group, an amino group, or a cyano group, but are each preferably a hydrogen atom or a methyl group. Further, $R^6$ and $R^7$ optionally represent the same group or different groups, but preferably represent the same group.

Examples of the halogen compound having $R^1$ and $R^2$ that are both the same group represented by —O—C(=O)—

NH—$R^5$ and $R^5$ that is a phenyl group include a halogen compound represented by formula (7) below.

(7)

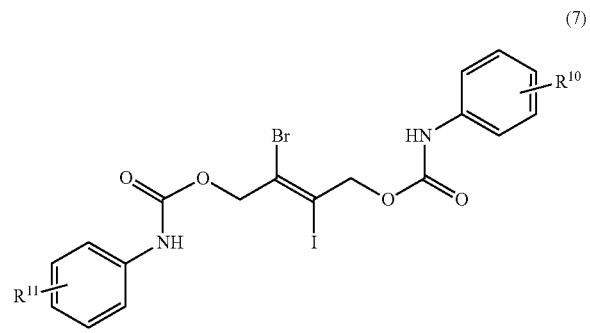

$R^{10}$ and $R^{11}$ in formula (7) above may be each a hydrogen atom, a methyl group, a hydroxy group, a methoxy group, a carboxyl group, an amino group, or a cyano group, but are each preferably a hydrogen atom or a methyl group. Further, $R^{10}$ and $R^{11}$ optionally represent the same group or different groups, but preferably represent the same group.

Hereinafter, a method for producing a diphenyl ether derivative in which $R^1$ and $R^2$ in the halogen compound represented by formula 3 above are both represented by formula —O—$R^3$, and $R^3$ therein is a phenyl group (a halogen compound represented by formula 8 below) will be exemplified using the halogen compound represented by formula 4 above.

(8)

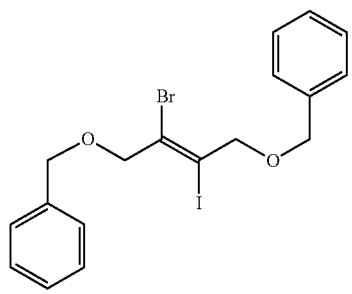

<<Synthesis of Diphenyl Ether Derivative (Formula 8)>>

50 g of toluene, 8.7 g of silver (I) oxide, 6.1 g of benzyl bromide, and 5.0 g of the halogen compound represented by formula 4 above were added to a reaction container equipped with a thermometer and a stirrer bar. Thereafter, the reaction was performed at an internal temperature of 40° C. for 24 hours. After the disappearance of the peak of the aforementioned halogen compound (formula 4) as a raw material was confirmed using a gas chromatograph (GC: device name: GC-2010, manufacturer: SHIMADZU CORPORATION), 10 g of methanol was added thereto, followed by stirring for 3 hours. Thereafter, the solvent was distilled off using an evaporator. After 40 g of ethyl acetate was added thereto, followed by stirring for 2 hours, the precipitated black solid was separated by filtration. After the solvent was again removed using an evaporator, 50 g of IPA was added thereto, followed by stirring at an internal temperature of 5 to 10° C. overnight. The precipitated solid was separated by filtration, followed by drying, to obtain 1.43 g of a white solid (yield: 17.7%). It was confirmed to be the diphenyl ether derivative represented by formula 8 above, by confirming the presence of a peak derived from an ether bond at 1243 cm$^{-1}$ and the disappearance of a broad peak derived from an OH group detected around 3200 to 2800 cm$^{-1}$ using an infrared absorption spectrum (IR: device name: Frontier GOLD spotlight 400, manufacturer: Perkin Elmer).

Hereinafter, a method for producing a distearyl ether derivative (halogen compound represented by formula 9 below) in which $R^1$ and $R^2$ in the halogen compound represented by formula 3 above are both represented by formula —O—$R^3$, and $R^3$ therein is a stearyl group will be exemplified using the halogen compound represented by formula 4 above.

(9)

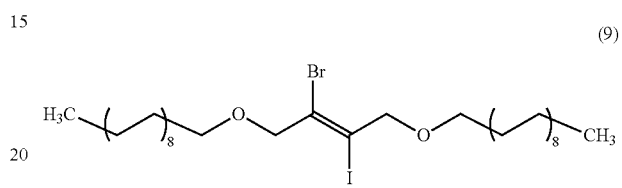

<<Synthesis of Distearyl Ether Derivative (Formula 9)>>

It was synthesized by the same procedures as in the reaction conditions for the synthesis of the diphenyl ether derivative represented by formula 8 above except that 6.13 g of benzyl bromide was changed to 12.0 g of 1-bromooctadecane. Thereby, 1.68 g of a white solid (yield: 12.8%) was obtained. It was confirmed to be the distearyl ether derivative represented by formula 9 above by confirming the presence of a peak derived from an ether bond at 1231 cm$^{-1}$, the presence of peaks due to C—H stretching at 2850 and 2960 cm$^{-1}$, and further the disappearance of a broad peak derived from an OH group detected around 3200 to 2800 cm$^{-1}$, using an infrared absorption spectrum (IR).

Hereinafter, a method for producing a diphenyl ester derivative (halogen compound represented by formula 10 below) in which $R^1$ and $R^2$ in the halogen compound represented by formula 3 above are both represented by formula —O—C(═O)—$R^4$, and $R^4$ therein is a phenyl group will be exemplified using the halogen compound represented by formula 4 above.

(10)

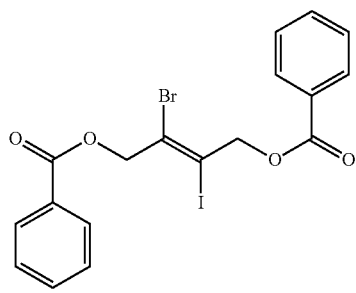

<<Synthesis of Diphenyl Ester Derivative (Formula 10)>>

50 g of toluene, 3.6 g of triethylamine, 0.21 g of 4,4-dimethylamino pyridine (DMAP), and 5.0 g of the halogen compound represented by formula 4 above were added to a reaction container equipped with a thermometer and a stirrer bar. A solution obtained by dissolving 4.27 g of benzoyl chloride in 10 g of toluene was added dropwise thereto over 15 minutes. After the completion of the dropwise addition, the reaction was performed at an internal temperature of 40°

C. for 72 hours. After the disappearance of the peak of the aforementioned halogen compound (formula 4) as a raw material was confirmed using a gas chromatograph (GC: device name: GC-2010, manufacturer: SHIMADZU CORPORATION), 50 g of pure water was added thereto. After stirring for 5 minutes, the lower layer was removed, and 50 g of pure water was again added thereto, followed by liquid separation. The solvent in the upper layer was distilled off using an evaporator, to obtain a highly viscous liquid. 70 g of IPA and 1 g of toluene were added thereto, followed by stirring, and a solid content was precipitated. It was stirred at room temperature overnight, as it was. The precipitated solid was separated by filtration, followed by drying, to obtain 4.51 g of a white solid (yield: 52.7%). It was confirmed to be the diphenyl ester derivative represented by formula 10 above by confirming the presence of a peak derived from an ester bond at 1742 cm$^{-1}$ and the disappearance of a broad peak derived from an OH group detected around 3200 to 2800 cm$^{-1}$ using an infrared absorption spectrum (IR: device name: Frontier GOLD spotlight 400, manufacturer: Perkin Elmer).

Hereinafter, a method for producing a distearyl ester derivative (halogen compound represented by formula 11 below) in which $R^1$ and $R^2$ in the halogen compound represented by formula 3 above are both represented by formula —O—C(=O)—$R^4$, and $R^4$ therein is a stearyl group will be exemplified using the halogen compound represented by formula 4 above.

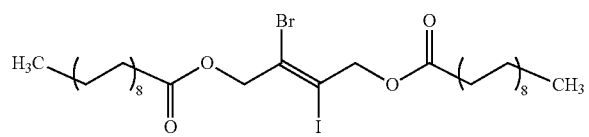

(11)

<<Synthesis of Distearyl Ester Derivative (Formula 11)>>

It was synthesized by the same procedures as in the reaction conditions for the synthesis of the diphenyl ester derivative represented by formula 10 above except that 4.27 g of benzoyl chloride was changed to 10.36 g of stearyl chloride. Thereby, 9.14 g of a white solid (yield: 64.8%) was obtained. It was confirmed to be the stearyl ester derivative represented by formula 11 above by confirming the presence of a peak derived from an ester bond at 1742 cm$^{-1}$, the presence of peaks due to C—H stretching at 2850 and 2960 cm$^{-1}$, and further the disappearance of a broad peak derived from an OH group detected around 3200 to 2800 cm$^{-1}$, using an infrared absorption spectrum (IR).

Hereinafter, a method for producing a diphenyl urethane derivative (halogen compound represented by formula 12) in which $R^1$ and $R^2$ in the halogen compound represented by formula 3 above are both represented by —O—C(=O)—NH—$R^5$, and $R^5$ therein is a phenyl group will be exemplified using the halogen compound represented by formula 4 above.

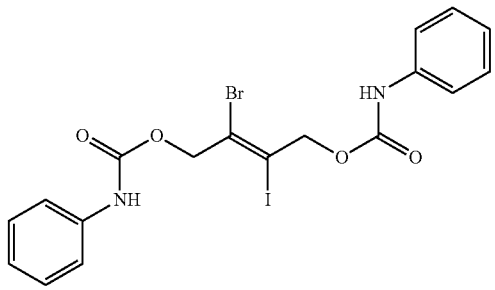

(12)

<<Synthesis of Diphenyl Urethane Derivative (Formula 12)>>

50 g of cyclohexane, 10 g of toluene, 0.1 g of 1,4-diazabicyclo[2.2.2]octane (DABCO), 4.47 g of phenyl isocyanate, and 5.0 g of the halogen compound represented by formula 4 above were added to a reaction container equipped with a thermometer and a stirrer bar. Thereafter, the reaction was performed at an internal temperature of 65° C. for 24 hours. After the disappearance of the peak of the aforementioned halogen compound as a raw material was confirmed by GC, 20 g of methanol was added thereto, and the reaction was performed at room temperature overnight. The precipitated solid was separated by filtration. IPA was added to the solid separated by filtration, followed by stirring for 3 hours. It was again separated by filtration, to obtain 6.27 g of a white solid (yield: 69.2%). It was confirmed to be the diphenyl urethane derivative represented by formula 12 above by confirming the presence of a peak derived from the N—H stretching vibration of N–1 substituted amide at 3317 cm$^{-1}$, the presence of a peak derived from an urethane bond at 1708 cm$^{-1}$, the disappearance of peaks derived from isocyanate appearing around 2275 to 2250 cm$^{-1}$, and the disappearance of a broad peak derived from an OH group detected around 3200 to 2800 cm$^{-1}$, using an infrared absorption spectrum (IR).

Hereinafter, a method for producing a distearyl urethane derivative (halogen compound represented by formula 13) in which $R^1$ and $R^2$ in the halogen compound represented by formula 3 above are both represented by —O—C(=O)—NH—$R^5$, and $R^5$ therein is a stearyl group will be exemplified using the halogen compound represented by formula 4 above.

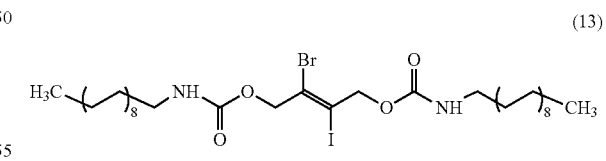

(13)

<<Synthesis of Distearyl Urethane Derivative (Formula 13)>>

It was synthesized by the same procedures as in the reaction conditions for the synthesis of the diphenyl urethane derivative represented by formula 12 above except that 4.47 g of phenyl isocyanate was changed to 7.57 g of stearyl isocyanate, and the amount of the halogen compound represented by formula 4 above was changed from 5.0 g to 3.0 g. Thereby, 9.14 g of a white solid (yield: 64.8%) was obtained. It was confirmed to be the distearyl urethane derivative represented by formula 13 above by confirming the presence of a peak derived from N—H stretching vibration of N-1 substituted amide at 3346 cm$^{-1}$, the presence of peaks due to C—H stretching at 2849 and 2917 cm$^{-1}$, the presence of a peak derived from an urethane bond at 1688 cm$^{-1}$, the presence of a peak derived from chain N-1 substituted amide at 1528 cm$^{-1}$, the disappearance of a peak derived from isocyanate appearing around 2275 to 2250 cm$^{-1}$, and the disappearance of a broad peak derived from an OH group detected around 3200 to 2800 cm$^{-1}$, using an infrared absorption spectrum (IR).

Next, a flux containing the aforementioned activator of this embodiment will be described.

The application of the flux of this embodiment is not specifically limited, and can be used, for example, as a flux or a post flux for soldering such as a solder paste and a flux-cored solder.

In the flux of this embodiment, one of the aforementioned activators may be used or two or more of them may be mixed for use. The content of the activator in the flux is not specifically limited, but is, for example, 0.1 mass % or more and 10 mass % or less, preferably 0.3 mass % or more and 4 mass % or less. In the case of using the flux of this embodiment as a flux for flux-cored solders, the content of the activator is, for example, 0.3 mass % or more and 4 mass % or less, preferably 1 mass % or more and 3 mass % or less. When the content of the activator falls within the aforementioned range, the solder wettability is easily improved immediately after soldering, and the solder wettability is easily continuously improved, which is therefore preferable.

Other than the aforementioned activator of this embodiment, the flux of this embodiment may contain a known activator component as an auxiliary activator. As such an auxiliary activator, an organic acid or an amine halogen salt, for example, can be used. Examples of the organic acid include glutaric acid, adipic acid, azelaic acid, sebacic acid, stearic acid, and benzoic acid. Further, examples of the amine of the amine halogen salt include diethylamine, dibutylamine, tributylamine, diphenylguanidine, and cyclohexylamine. Examples of the corresponding halogen include fluorine, chlorine, bromine, iodine, and astatine, where fluorine is not desirable because of its high corrosivity, which may cause a reduction in the reliability. Further, astatine is classified as a halogen, but it is not practical because it has a considerably short radioactive half-life and can exist only in a reactor.

The flux of this embodiment may contain a resin component, a solvent component, or the like. The resin component is not specifically limited, as long as it is a known resin component used as a resin component for fluxes such as a synthetic resin and a natural resin. Examples thereof include polymerized rosin, hydrogenated rosin, natural rosin, disproportionated rosin, and acid-modified rosin.

The content of the aforementioned resin component in the flux is not specifically limited, but is, for example, 20 mass % or more and 99 mass % or less, preferably 30 mass % or more and 99 mass % or less. In the case of using the flux of this embodiment as a flux for flux-cored solders, the content of the resin component is, for example, 40 mass % or more and 99 mass % or less, preferably 60 mass % or more and 99 mass % or less.

The solvent component is not specifically limited, as long as it is a known component used as a solvent component for fluxes. Examples thereof include glycol ethers such as diethylene glycol monohexyl ether (hexyl diglycol), diethylene glycol dibutyl ether (dibutyl diglycol), diethylene glycol mono 2-ethylhexyl ether (2 ethylhexyl diglycol), and diethylene glycol monobutyl ether (butyl diglycol); aliphatic compounds such as n-hexane, isohexane, and n-heptane; esters such as isopropyl acetate, methyl propionate, and ethyl propionate; ketones such as methyl ethyl ketone, methyl-n-propyl ketone, and diethyl ketone; and alcohols such as ethanol, n-propanol, isopropanol, and isobutanol. The solvent can be used alone, or a plurality of types can be mixed for use.

The content of the aforementioned solvent component in the flux is not specifically limited, but is, for example, 0 mass % or more and 60 mass % or less, preferably 0 mass % or more and 40 mass % or less.

The flux of this embodiment may further contain additives such as a thixotropic agent, an antioxidant, a surfactant, a defoamer, and a corrosion inhibitor.

Further, a solder containing the flux of this embodiment will be described. As described above, the flux of this embodiment can be used for solder compositions such as a solder paste, solders such as flux-cored solder, or the like.

The solder paste as a solder composition is configured by mixing a solder alloy powder with the aforementioned flux of this embodiment. The solder alloy is not specifically limited, and either lead-free solder alloys or lead-containing solder alloys can be employed, but lead-free solder alloys are preferable in view of environmental impact. Specifically, examples of the lead-free solder alloys include alloys containing tin, silver, copper, zinc, bismuth, antimony, or the like, more specifically, include alloys of Sn/Ag, Sn/Ag/Cu, Sn/Cu, Sn/Ag/Bi, Sn/Bi, Sn/Ag/Cu/Bi, Sn/Sb, Sn/Zn/Bi, Sn/Zn, Sn/Zn/Al, Sn/Ag/Bi/In, Sn/Ag/Cu/Bi/In/Sb, In/Ag, or the like.

In the solder paste as a solder composition, the mixing amount of the aforementioned solder alloy powder is preferably 80 mass % or more and 95 mass % or less, and the mixing amount of the aforementioned flux is preferably 5 mass % or more and 20 mass % or less, for example.

The flux-cored solder as a solder is constituted by a thin cylindrical solder alloy with its center portion filled with the flux of this embodiment. The content of the flux in the flux-cored solder is preferably 1 mass % or more and 5 mass % or less. The flux containing the activator of this embodiment is particularly preferably used as a flux for flux-cored solders. When the wettability of a flux-cored solder is reduced, failure of fillet formation and failures such as a bridge between terminals and icicles tend to occur. Since the flux-cored solder containing the flux of this embodiment can suppress the reduction of the wettability immediately after soldering and can improve the wettability continuously, it can effectively reduce the aforementioned failures caused by the reduction of the wettability.

As described above, the present invention can improve the solder wettability immediately after soldering and can continuously improve the solder wettability.

Further, in the case where $X^1$ in formula 1 is Br or I, and $X^2$ therein is Br or I, the present invention can improve the solder wettability within a particularly short time from the soldering and can improve the solder wettability more continuously. In the present invention, the aforementioned case means that, when $X^1$ is Br, $X^2$ is I, and when $X^1$ is I, $X^2$ is Br.

The flux activator, the flux, and the solder composition according to the present embodiments are as described above, but it should be considered that the embodiments disclosed herein are merely examples in all respects and they are not restrictive. The scope of the present invention is defined by the appended claims rather than by the above description, and is intended to include meanings equivalent to the claims and all changes without departing from the claims.

EXAMPLES

Next, Examples of the present invention will be described together with Comparative Examples. It should be noted that the present invention is not construed as being limited to the following examples.

(Production of Flux)

Using the following activators 1 to 6 as activators, fluxes having the mixing ratios shown in Table 1 were produced. The raw materials were put into a heating container, followed by heating to 180° C., and it was confirmed that all the raw materials were dissolved and dispersed. Thereafter, it was cooled to room temperature, to obtain a uniform flux. Here, "KR-612" manufactured by ARAKAWA CHEMICAL INDUSTRIES, LTD. was used as a hydrogenated rosin, "PINECRYSTAL KE-604" manufactured by ARAKAWA CHEMICAL INDUSTRIES, LTD. was used as an acid-modified rosin, and adipic acid was used as an organic acid.

(Method for Testing Wettability)

The wettability of each flux was evaluated by the following method. A thread solder (solder alloy: SAC305 (96.5 mass % of Sn, 3.0 mass % of Ag, and

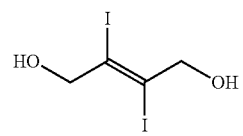

(15)

0.5 mass % of Cu) with a length of about 7 mm and a diameter of 1.0 mm) formed into a 2.0-mm diameter ring was placed on a degreased and cleaned copper plate (3 mm×3 mm×0.5 mm-thick), and a piece (about 10 mg) of each flux was put on the ring-shaped thread solder, to produce a test piece. Each test piece was placed on a solder bath heated to 300° C., to melt the thread solder. After a lapse of 5 seconds from the melting, the test piece was detached from the solder bath. The flux of the test piece was washed with isopropyl alcohol, and the height of the solder

TABLE 1

|  | Ex. 1 | Ex. 2 | Ex. 3 | Ex. 4 | Ex. 5 | Ex. 6 | Ex. 7 | C. Ex. 1 | C. Ex. 2 |
|---|---|---|---|---|---|---|---|---|---|
| Hydrogenated rosin | 33 | 33 | 33 | 33 | 33 | 33 | 33 | 33 | 33 |
| Acid-modified rosin | 63.5 | 63.5 | 63.5 | 63.5 | 63.5 | 63.5 | 63.5 | 63.5 | 63.5 |
| Organic acid | 1.5 | 1.5 | 1.5 | 1.5 | 1.5 | 1.5 | 1.5 | 1.5 | 1.5 |
| Activator 1 (Formula (4)) | 2 | | | | | | | | |
| Activator 2 (Formula (8)) | | 2 | | | | | | | |
| Activator 3 (Formula (9)) | | | 2 | | | | | | |
| Activator 4 (Formula (10)) | | | | 2 | | | | | |
| Activator 5 (Formula (11)) | | | | | 2 | | | | |
| Activator 6 (Formula (12)) | | | | | | 2 | | | |
| Activator 7 (Formula (13)) | | | | | | | 2 | | |
| Activator 8 (Formula (14)) | | | | | | | | 2 | |
| Activator 9 (Formula (15)) | | | | | | | | | 2 |
| Total | 100 | 100 | 100 | 100 | 100 | 100 | 100 | 100 | 100 |

Unit: mass %
Activator 1: Halogen compound represented by formula 4 above
Activator 2: Diphenyl ether derivative represented by formula 8 above
Activator 3: Distearyl ether derivative represented by formula 9 above
Activator 4: Diphenyl ester derivative represented by formula 10 above
Activator 5: Distearyl ester derivative represented by formula 11 above
Activator 6: Diphenyl urethane derivative represented by formula 12 above
Activator 7: Distearyl urethane derivative represented by formula 13 above
Activator 8: Halogen compound represented by formula 14 below
Activator 9: Halogen compound represented by formula 15 below

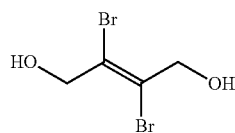

(14)

was measured using a micrometer (manufactured by MITUTOYO CORPORATION). The spreading ratio was determined from the height of the solder by the following calculation formula.

Spreading ratio (%)=100×(D−H)/D

H: Height of solder=(Substrate thickness after test)−(Substrate thickness before test)
D: Diameter (mm) when regarding solder used for test as sphere=2.2 (mm)

Further, the solder of each test piece was observed by visual inspection, and the state of the solder was evaluated. The case where no dewetting was observed was evaluated as ○, and the case where dewetting was observed was evaluated as x. Table 2 shows the results.

TABLE 2

|  | Ex. 1 | Ex. 2 | Ex. 3 | Ex. 4 | Ex. 5 | Ex. 6 | Ex. 7 | C. Ex. 1 | C. Ex. 2 |
|---|---|---|---|---|---|---|---|---|---|
| Spreading ratio | 81.2% | 78.4% | 78.6% | 79.9% | 77.0% | 77.8% | 78.1% | 73.4% | 76.1% |
| Solder state (dewetting) | ○ | ○ | ○ | ○ | ○ | ○ | ○ | x | x |

As shown in Table 2, it was obvious that Examples 1 to 7 had high spreading ratio and less dewetting, that is, high wettability, as compared with Comparative Examples 1 and 2. In Examples 2 to 7, the spreading ratio was slightly low, as compared with Example 1. This is probably because the activator in which a substituent having high molecular weight was introduced was used, and thus the halogen content ratio was reduced.

(Method for Testing Soldering)

Next, using the fluxes using the aforementioned activators 1 to 7 (Examples 1 to 7 and Comparative Examples 1 and 2), flux-cored solders (Examples 8 to 14 and Comparative Examples 3 and 4) were produced and were subjected to a soldering test. Each flux-cored solder was produced with the content of the flux adjusted to 3.2% and the wire diameter thereof adjusted to 0.5 mm.

Using the flux-cored solder, slide soldering was performed. Using an FR-4 substrate with a thickness of 1.6 mm, 20 through holes with a diameter of 1.0 mm were formed in series. The leads composed of L-angle pins (20 pins, plated with Ni/Au) were inserted into the through holes. Using a soldering robot (UNIX-412R, manufactured by Japan Unix Co., Ltd.), an iron tip (split shape, P1V10-23) set at 350° C. was slid on the pins in series (at a speed of 6 mm/second and 10 mm/second), and the aforementioned flux-cored solder was fed to the iron tip at the same time. The flux-cored solder was heated and melted by the iron tip, and the wetting spreads due to the flux, to form a solder joint between a lead and a land of the substrate. Evaluation was performed as follows.

<<Observation of Fillet>>

The state where the land of the substrate was wetted by the solder, to form a solder joint in the periphery of the lead of the pin part like the foot of a mountain was referred to as the state where a fillet was formed. Each substrate was observed by visual inspection. The case where every pad of the substrate was wetted by the solder to provide a good state was evaluated as A, the case where a cold solder joint occurred was evaluated as B, and the case where dewetting of the solder partially occurred on the pad of the substrate thereby forming non-uniform fillet shape was evaluated as C. The state with a cold solder joint occurring means the state where, although the land was wetted by the solder, the shape was not like the foot of a mountain and was like a ball.

<<Observation of Bridge>>

A bridge is a failure phenomenon in which the oxide film on the surface of the solder was not sufficiently removed, resulting in a decrease in fluidity, so that the solder becomes continuous with an adjacent pin. Each substrate was observed by visual inspection. The case where no bridge was present with high slide speed (10 mm/second) was evaluated as A, the case where a bridge was present with high slide speed (10 mm/second) though no bridge was present with normal slide speed (6 mm/second) was evaluated as B, and the case where a bridge was present with normal slide speed (6 mm/second) was evaluated as C. Table 3 shows the results.

TABLE 3

|  | Ex. 8 | Ex. 9 | Ex. 10 | Ex. 11 | Ex. 12 | Ex. 13 | Ex. 14 | C. Ex. 3 | C. Ex. 4 |
|---|---|---|---|---|---|---|---|---|---|
| Observation of fillet | A | A | A | A | A | B | B | C | B |
| Observation of bridge | A | B | B | B | B | B | B | C | C |

Examples were good in both fillet formation and bridge occurrence, as compared to Comparative Examples. In particular, Example 8 was evaluated as A in both fillet formation and bridge occurrence, and it was obvious that the soldering could be performed very well.

The invention claimed is:

1. A flux activator comprising a halogen compound represented by formula 1 below:

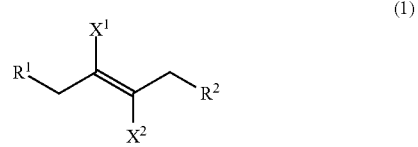

(1)

where $X^1$ and $X^2$ represent different halogen atoms, $R^1$ and $R^2$ are each a group represented by any one of formulas —OH, —O—$R^3$, —O—C(=O)—$R^4$, and —O—C(=O)—NH—$R^5$, $R^1$ and $R^2$ optionally represent the same group or different groups, $R^3$, $R^4$, and $R^5$ are each an aromatic hydrocarbon group having 1 to 18 carbon atoms or an aliphatic hydrocarbon group having 1 to 18 carbon atoms, and $R^3$, $R^4$, and $R^5$ optionally represent the same group or different groups, wherein $X^1$ and $X^2$ are each any of Br, Cl and I, $X^2$ is I when $X^1$ is Br or Cl, and $X^2$ is Br or Cl when $X^1$ is I.

2. A flux comprising the flux activator according to claim 1.

3. A solder comprising the flux according to claim 2.

* * * * *